(12) United States Patent
Staples et al.

(10) Patent No.: US 8,420,133 B2
(45) Date of Patent: Apr. 16, 2013

(54) MODIFIED PECTINS, COMPOSITIONS AND METHODS RELATED THERETO

(75) Inventors: Mark Staples, Cambridge, MA (US); James Rolke, San Diego, CA (US)

(73) Assignee: La Jolla Pharmaceutical Company, San Diego, CA (US)

( * ) Notice: Subject to any disclaimer, the term of this patent is extended or adjusted under 35 U.S.C. 154(b) by 0 days.

(21) Appl. No.: 13/588,877

(22) Filed: Aug. 17, 2012

(65) Prior Publication Data

US 2012/0315309 A1 Dec. 13, 2012

Related U.S. Application Data

(60) Continuation of application No. 13/400,007, filed on Feb. 17, 2012, which is a division of application No. 11/093,268, filed on Mar. 28, 2005, now Pat. No. 8,128,966.

(60) Provisional application No. 60/556,674, filed on Mar. 26, 2004.

(51) Int. Cl.
*A01N 65/00* (2009.01)

(52) U.S. Cl.
USPC .......................................................... 424/725

(58) Field of Classification Search ........................ None
See application file for complete search history.

(56) References Cited

U.S. PATENT DOCUMENTS

| | | | |
|---|---|---|---|
| 2,444,266 | A | 6/1948 | Owens et al. |
| 2,503,258 | A | 4/1950 | Graham et al. |
| 4,016,351 | A | 4/1977 | Eschinasi |
| 5,498,702 | A | 3/1996 | Mitchell et al. |
| 5,547,945 | A | 8/1996 | Ye et al. |
| 5,569,483 | A | 10/1996 | Timonen et al. |
| 5,834,442 | A | 11/1998 | Raz et al. |
| 5,895,784 | A | 4/1999 | Raz et al. |
| 6,500,807 | B1 | 12/2002 | Platt et al. |
| 2003/0013681 | A1 | 1/2003 | Chang et al. |
| 2003/0100535 | A1 | 5/2003 | Chang et al. |
| 2005/0008572 | A1 | 1/2005 | Prokop et al. |

FOREIGN PATENT DOCUMENTS

| | | |
|---|---|---|
| DE | 143-261 | 8/1980 |
| JP | 55-52301 | 4/1980 |
| JP | 63-89501 | 4/1988 |
| WO | WO 96/01640 | 1/1996 |
| WO | WO 97/34907 | 9/1997 |
| WO | WO 00/07624 | 2/2000 |
| WO | WO 00/62076 | 10/2000 |
| WO | WO 02/057284 | 7/2002 |
| WO | WO 2004/091634 | 10/2004 |

OTHER PUBLICATIONS

International Search Report for Application No. PCT/US2005/010504 dated Jun. 27, 2005.
Curti, "Physical Barriers to Drug Delivery in Tumors," Critical Reviews in Oncology/Hematology, 14:29-39 (1993).
Devita et al., "Cancer: Principles and Practices of Oncology," 5th Edition, Chapter 7 pp. 139, 143-146 (1997).
Dumont et al.. "Inhibition of Experimental Metastasis and Cell Adhesion of B16F1 melanoma Cells by Inhibitors of protein Kinase C," Cancer Research, 52:1195-1200 (1992).
Fidler et al., Biological Behavior of Malignant Melanoma Cells Correlated to Their Survival in Vivo, Cancer Research, 35:218-224 (1975).
Finne et al., Lectin-Resistant Variants and Revertants of Mouse Melanoma Cells: Differential Expression of a Fucosylated Cell-Surface Antigen and Altered Metastasizing Capacity, *Int. J. Cancer*, 43:300-304 (1989).
Franz, Structure-activity Relation of Polysaccharides With Antitumor Activity, *Chem. Abstract*, 108:20. Ref. #31318n (1998).
Hosoda et al., "Changes of Diamine Oxidase Activity in Intraintestinal Nutrition in Rats—Studies on the Effect of Pectin Addition and of Anti-Cancer Drug," *Chem. Abstract*, #6827m, 110:635, Ref. #6827m (1989).
Jain, "Barriers to Drug Delivery in Solid Tumors," *Scientific American*, 58-65 (1994).
Mueller et al., "Biochemical Characterization of a Component in Extracts of Viscum Album Enhancing Human NK Cytotoxicity," *Chem. Abstract*, 110:44 Ref. #165780 (1999). (Immunopharacology 1989, 17(i), 11-18).
Neff et al., "Inhibitory Effects of a Pectin-Enriched Tomato Cell Wall Fraction on *Agrobacterium tumefeciens* Binding and Tumor Formation," *Plant Physiol.*, 83:525-528 (1987).
Osband et al, "Problems in the Investigational Study and Clinical Use of Cancer Immunotherapy," *Immunology Today*, 11(6):193-195 (1992).
Pall Life Sciences, "Minimate Tangential Flow Filtration System and Minimate TFF Capsule," 4 pages (2004).
Platt et al., Modulation of the Lung Colonization of B16-F1 Melanoma Cells by Citrus Pectin, J. Natl. Cancer Inst., 84(6):438-442 (1992).
Shultz et al., "Inhibition by Human Recombinant Tissue Inhibitor of Metalloproteinases of Human amnion Invasion and Lung Colonization by Murine B16-F10 Melanoma Cells," *Cancer Research*, 48:5539-5545 (1988).
Siemann, "Satisfactory and Unsatisfactory Tumor Models: Factors Influencing the Selection of a Tumor Model for Experimental Evaluation", Rodent Tumor Models in Experimental Cancer Therapy, Published 1987 by Pergamon Press (NY), pp. 12-14.
Trott, "Differences Between Mouse and Human Tumors that Affect Their Responses to Radiotherapy," Rodent Tumor Models in Experimental Cancer Therapy, Published 1987 by Pergamon Press (NY) 7 pages.

*Primary Examiner* — Michael Meller
(74) *Attorney, Agent, or Firm* — Ropes & Gray LLP

(57) ABSTRACT

The present invention provides compositions of modified pectin and methods for preparing and using them.

22 Claims, 4 Drawing Sheets

MODIFIED PECTINS, COMPOSITIONS AND METHODS RELATED THERETO

CROSS-REFERENCE TO RELATED APPLICATIONS

This application is a continuation of U.S. application Ser. No. 13/400,007, filed Feb. 17, 2012, which is a divisional of U.S. application Ser. No. 11/093,268, filed Mar. 28, 2005, which claims the benefit of U.S. Provisional App. No. 60/556,674 filed Mar. 26, 2004, the disclosure of which are incorporated by reference in their entirety.

FIELD OF THE INVENTION

The invention relates in general to the fields of polysaccharide chemistry and oligosaccharide chemistry, and more particularly to the chemistry of naturally-occurring pectins and methods for making and using modified pectins.

BACKGROUND OF THE INVENTION

Modified pectins have long been recognized as being useful in suppressing the metastasis of cancer cells. This effect is thought to be due to binding of the modified pectin to galectins, in particular galectin-3, and possibly to other as-yet unidentified saccharide-binding cell surface receptors. Several compositions of modified pectins have been described. See Platt et al. "Modulation of Lung Colonization of B16-F1 Melanoma Cells by Citrus Pectin" *J. Natl. Cancer Inst.* 84(6): 438-442 (1992); Inohara et al. "Effects of Natural Complex Carbohydrate (citrus pectin) on Murine Melanoma Cell Properties Related to Galectin-3 function" *Glycoconjugate J.* 11:527-532 (1994); Pienta et al. "Inhibition of spontaneous metastasis in a Rat Prostate Cancer Model by Oral Administration of Modified Citrus Pectin" J. Natl. Cancer Inst. 87:348-353 (1995); U.S. patent application Ser. Nos. 08/024,487, 08/819,356, 2003/0013682, 2003/0004132, and 2002/0107222, and U.S. Pat. Nos. 6,423,314, 5,681,923, 5,834,442, and 5,895,784. The disclosures of each of these applications and patents are incorporated herein by reference in their entirety. Synthetic carbohydrate derivatives have also been reported to bind to and block galectin-3. See PCT application WO 02/057284.

Examples of modified pectins of the type described previously are described by formulas I-IV below:

-[α-D-GalpA-(1→4)-α-D-GalpA]$_n$-      (I)

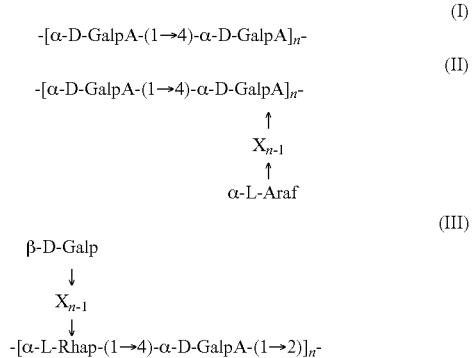

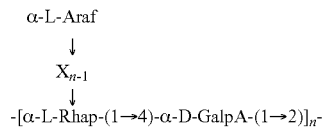

In the above representations, n is an integer greater than 1, $X_{n-1}$ represents a short side-chain of neutral sugar residues, Galp is galactose, Rhap is rhamnose, GalpA is galacturonic acid and Araf is arabinose. X can be any of several sugars found in pectin side chains, including but not limited to β-Apif, β-Rhap, α-Fucp, β-GlcpA, α-GalpA, β-GalpA, β-DhapA, Kdop, β-Acef, α-Galp, and α-Arap.

The existing methods used to prepare modified pectins generally suffer from poorly controlled chemical processes and difficult product isolation and purification processes. These factors either separately or combined typically result in widely varying therapeutic activities, molecular weights, polydispersities, concentrations, monosaccharide compositions, linkage makeup, potency and impurity profiles. Many of these processes employ organic solvents, which can create explosion hazards and toxicological effects from residual solvent and require expensive disposal of solvent waste.

SUMMARY OF THE INVENTION

The invention provides modified pectin compositions and methods of producing and using them. The modified pectin compositions described herein may have improved potency, purity and composition uniformity, and the methods of manufacture permit these benefits to be achieved reliably and reproducibly. In certain embodiments, the modified pectin compositions are substantially free of ethanol and acetone (e.g., have less than 1% of either or both solvents).

In certain embodiments, the modified pectin consists essentially of a backbone comprising homogalacturonan and/or rhamnogalacturonan I, having neutral sugar side chains and a low degree of neutral sugar branching dependent from the backbone. In certain embodiments, the modified pectin is de-esterified and partially depolymerized, so as to have a disrupted rhamnogalacturonan backbone. The compositions are preferably aqueous solutions containing at least 0.5%, 1%, 5% or 10% by weight of the modified pectin, e.g., up to about 10% or 15% by weight. In another embodiment, the modified pectin forms a colloidal solution in water. The size of the colloidal particles may be less than 1 μm in diameter, preferably less than 0.65 μm, and most preferably less than 0.2 μm.

The invention also provides methods for manufacturing modified pectin, comprising one or more of the following steps: partially depolymerizing a pectin polymer by disrupting the rhamnogalacturonan/homogalacturonan backbone, de-esterifying galacturonic acid moieties in the backbone, breaking down side chains of neutral sugars, and optionally creating and/or isolating a colloidal suspension of the resulting product in water. In certain embodiments, the process of the invention provides a substantially ethanol- and acetone-free product suitable for parenteral or oral administration.

The present invention relates in part to a modified pectin material that inhibits cancer cell proliferation with an $IC_{50}$ less than 100 μg/mL, less than 75 μg/mL, less than 50 μg/mL, e.g., with an $IC_{50}$ in the range of 25-100 μg/mL, 25-75 μg/mL, or 30-50 μg/mL, or even less than 1 μg/mL, e.g., with an $IC_{50}$ in the range of nanograms/mL.

The present invention further relates to a composition comprising a modified pectin material, such as a de-esterified and partially depolymerized modified pectin, substantially free of modified pectins having molecular weights below 25 kD.

The present invention further relates to a modified pectin made by passing modified or unmodified (commercial) pectin through a tangential flow filter, e.g., a filter having a pore size below 1, 0.65, 0.45, or 0.22 μm, such as a 0.2 μm filter. The pectin may be filtered as an aqueous solution (e.g., at a concentration of 1 to 20 mg/mL, preferably 3-8 mg/mL, most preferably 4-6 mg/mL) comprising 0-25%, preferably 10-20%, w/w ethanol. The solution may have a pH in the range of 2.5 to 10, preferably 3.0-7.5, most preferably 5.0 to 7.0.

In certain embodiments, the present invention provides a method for producing a modified pectin comprising partially depolymerizing a pectin polymer by disrupting homogalacturonan and/or rhamnogalacturonan backbones of the pectin polymer, de-esterifying galacturonic acid moieties in the backbone, breaking down side chains of neutral sugars into low molecular weight sugars, and collecting material remaining after ultrafiltration using a filter having a nominal 30 kD cutoff.

A modified pectin material as described herein preferably has an average molecular weight from 50-200 kD, 70-175 kD, 70-150 kD, 80-150 kD, or even 80-100 kD as measured by Gel Permeation Chromatography (GPC) with Multi Angle Laser Light Scattering (MALLS) detection.

A modified pectin as described or produced herein may consist essentially of a homogalacturonan backbone with small amounts of rhamnogalacturonan therein, wherein the backbone has neutral sugar side chains having a low degree of branching dependent from the backbone. In certain embodiments, the galacturonic acid subunits of the backbone are partially de-esterified, and in particular embodiments, the galacturonic acid subunits of the backbone are substantially de-esterified.

The compositions as described or produced herein may be formulated as pharmaceutical composition further comprising a pharmaceutically acceptable excipient. Such compositions may be aqueous solutions of modified pectin at a concentration of at least 0.5, 1, 5, or even 10 mg/mL, e.g., 0.5-10, 1-10, 5-10 mg/mL. Other forms include oral dosage forms, topical dosage forms, and inhalable formulations, such as inhalers comprising a modified pectin as described herein.

In another aspect, the present invention provides a process for manufacturing a de-esterified and partially depolymerized modified pectin, comprising providing a slurry of pectin in a water-miscible organic solvent (such as ethanol), combining the slurry with water to dissolve the pectin and form a solution, and treating the resulting solution with acid, base, or both to break down the pectin.

In yet another aspect, the present invention provides a process for manufacturing a de-esterified and partially depolymerized modified pectin, comprising treating a solution of pectin with acid, base, or both to break down the pectin, neutralizing the solution, and purifying a solution of the modified pectin by ultrafiltration (such as by tangential flow filtration).

In another aspect, the present invention provides a process for manufacturing a de-esterified and partially depolymerized modified pectin, comprising maintaining a solution at an alkaline pH between 9 and 12 (e.g., from 10 to 11) for up to 4 hours, lowering the pH of the solution to an acidic pH between 2 and 5 (e.g., from 2.5 to 3.5) for up to several days, and neutralizing the solution.

The present invention further relates to a method of producing modified pectin by passing modified (e.g., physically, chemically, and/or biologically-modified pectin as described herein) or unmodified (commercial) pectin through a tangential flow filter, e.g., a filter having a pore size below 1.0, 0.65, 0.45, or 0.22 μm, such as a 0.2 μm filter. The pectin may be filtered as an aqueous solution (e.g., at a concentration of 1 to 20 mg/mL, preferably 3-8 mg/mL, most preferably 4-6 mg/mL) comprising 0-25%, preferably 10-20%, w/w ethanol. The solution may have a pH in the range of 2.5 to 10, preferably 3.0-7.5, most preferably 5.0 to 7.0.

A process for producing modified pectin as described herein may further comprise precipitating modified pectin from the solution and washing the modified pectin with ethanol after neutralizing the solution and before purifying a solution of the modified pectin. Additional steps may include one or more of: adjusting the solution to iso-osmolality, clarifying the solution, subjecting a solution of the modified pectin to microfiltration, and lyophilizing the modified pectin. This process may further comprise treating the solution to reduce the concentration of endotoxins, and/or purifying a solution of the modified pectin by ultrafiltration to remove low molecular weight material.

The invention further relates to a modified pectin, such as de-esterified and partially depolymerized modified pectin produced by any method described herein, and pharmaceutical compositions thereof.

The present invention also provides pharmaceutical packages. In one such embodiment, a pharmaceutical package comprises a vial or ampoule containing a pharmaceutical composition comprising a modified pectin as described herein and a pharmaceutically acceptable excipient as an aqueous solution suitable for injection, and instructions for administering the composition to a patient in need thereof. In another embodiment, a pharmaceutical package comprises a plastic bag containing from 100 ml to 2 L of a pharmaceutical composition as described herein as a solution suitable for intravenous administration, and instructions for administering the composition to a patient in need thereof. In yet another embodiment, a pharmaceutical package comprises a solution of modified pectin as described herein and instructions for diluting the solution of modified pectin to a concentration suitable for administration to a patient intravenously or by injection. In still yet another embodiment, a pharmaceutical package comprises a pharmaceutical composition as described herein and instructions for diluting the composition to a concentration suitable for administration to a patient intravenously or by injection.

In still yet another aspect, the invention provides a method of inhibiting a cell proliferation process in a patient by administering a modified pectin material as described herein to a patient, thereby inhibiting cell proliferation in the patient. In certain embodiments, the cell proliferation process is angiogenesis or cancer, e.g., selected from renal cell cancer, Kaposi's sarcoma, chronic leukemia, chronic lymphocytic leukemia, breast cancer, sarcoma, myeloma, ovarian carcinoma, rectal cancer, throat cancer, melanoma, lymphoma, mesothelioma, colon cancer, bladder cancer, mastocytoma, lung cancer, liver cancer, mammary adenocarcinoma, pharyngeal squamous cell carcinoma, prostate cancer, pancreatic cancer, gastrointestinal cancer, and stomach cancer.

DETAILED DESCRIPTION OF THE INVENTION

I. Overview

Figure 1:
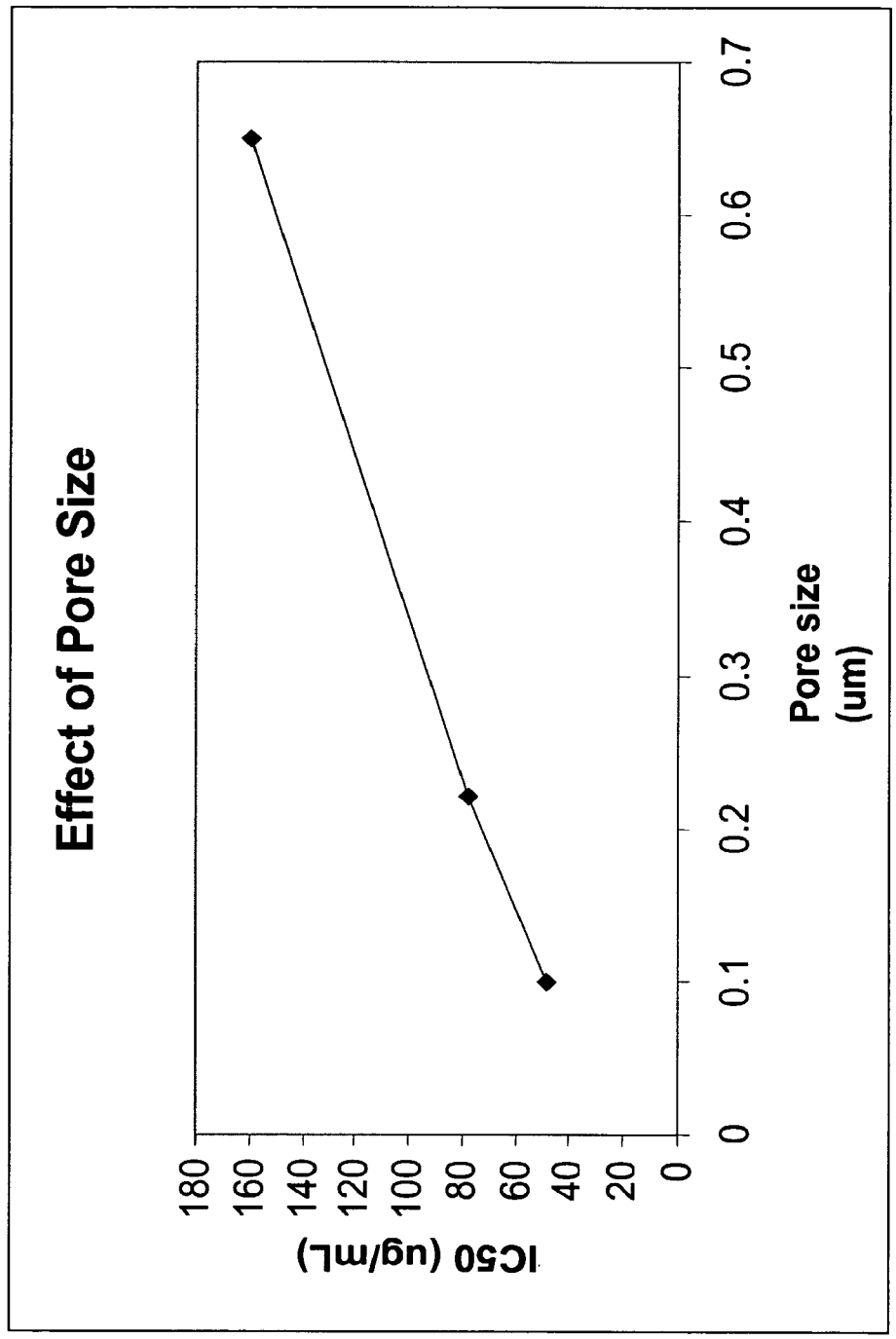
FIG. 1 demonstrates the effect of microfiltration pore size on therapeutic effectiveness.

The present invention discloses methods for the production of modified pectins with therapeutic effects, e.g., against cancer cells. As described herein, pectin can be modified by chemical, physical and/or biological, including enzymatic, means.

The invention also describes compositions composed in part or entirely of modified pectin that are suitable for the treatment of cancer. By way of example, useful compositions of modified pectin include dry powders, suspensions, gels or aqueous solutions. These compositions may consist essentially of modified pectin without any excipients, or they may be in combination with one or more pharmaceutically acceptable excipients.

A modified pectin composition of the present invention comprises or consists essentially of a homogalacturonan backbone with small amounts of rhamnogalacturonan I interspersed therein, with neutral sugar side chains, and has a low degree of neutral sugar branching dependent from the backbone. In certain embodiments, the modified pectin is de-esterified and partially depolymerized, so as to have a disrupted homogalacturonan backbone.

Modified pectin can be administered by any of a variety of routes. Examples of such delivery methods include oral suspensions, gels, and tablets, injectable solutions (intravenous, intraperitoneal), inhalable powders, and suspensions. Preferred compositions are aqueous solutions, oral tablets, and gels.

As used herein, the term "modified pectin" herein refers to any pectin that has been structurally modified, e.g., by chemical, physical, or biological (including enzymatic) means, or by some combination thereof. Non-limiting examples of such modification to the pectin structure include (but are not limited to) de-esterification, hydrolysis, oxidation and/or reduction of sugar moieties, functionalization of sugar moieties, conformational changes, and changes in molecular weight, linkage, and states of aggregation. In preferred embodiments, the structural modification includes one or more of de-esterification and hydrolysis. In other preferred embodiments, the structural modification includes reduction in particle size and/or aggregation states.

Modified pectin may be produced by chemical means, e.g., any chemical reaction or process that disrupts or changes chemical bonds of the pectin structure, such as covalent or ionic bonds. By way of example only, chemical bonding may be disrupted or formed by catalysis, hydrolysis, substitution, elimination, reduction, oxidation, and radical reactions. In certain embodiments, modified pectin according to the invention is produced by a process that includes hydrolysis, which is preferably catalyzed, e.g., by an acidic or basic reagent or both.

Pectin may also be modified by physical means. Physical means are meant to include non-chemical or -biological means that alter the structure of pectin. Such physical means include, but are not limited to heat, cold, freeze/thaw, irradiation, shear, ultra-high shear, use of cosolvents, and filtration.

Pectin may also be modified by biological means. Biological means are meant to include by way of example, enzymatic degradation of pectin. Finally, the invention contemplates the preparation of modified pectin by synthetic and/or recombinant methods. Like the production of recombinant proteins, complex polysaccharides might be engineered via a series of synthetic reactions or by recombinant methods.

In certain embodiments, pectin may be modified by a combination of the foregoing methods, such as chemical modification followed by physical or biological modification.

Typically, processes for making modified pectin result in a mixture of modified pectin and a number of impurities such as low molecular weight by-products, salts, co-solvents and inactive modified pectin. In certain embodiments of the invention, these impurities are acceptable and are not removed from the modified pectin. In other embodiments, the impurities are either reduced or removed entirely from the modified pectin composition. According to the invention, impurities can be removed by methods known in the art. By way of example, these methods include filtration, microfiltration, ultrafiltration, chromatography, centrifugation, extraction, drying, precipitation and dialysis. In certain preferred embodiments, the purification includes ultrafiltration.

Certain previously described processes of making modified pectin result in the formation of a modified pectin with a polydisperse molecular weight and particle size and low or varying degrees of therapeutic activity against cancer cell lines. In one embodiment of the invention, the polydispersity of the modified pectin is reduced to less than 5, preferably less than 4 or 3 and most preferably less than 2.5 to increase the modified pectin's effectiveness against cancer cell lines and, in turn, cancer. In preferred embodiments, the particle size polydispersity of the modified pectin is modified by microfiltration. In other preferred embodiments, the molecular weight polydispersity of the modified pectin is modified by ultrafiltration. In a certain embodiments, the modified pectin has an average particle size of less than 1 μm, preferably less than 0.65 μm and even more preferably less than 0.2 μm as measured by dynamic light scattering or atomic force microscopy.

In one embodiment, the method comprises the following acts or any subset thereof:

dissolving the pectin in water, e.g., at a concentration of 0.1 to 40 mg/mL, preferably 1 to 20 mg/mL, more preferably 5 to 15 mg/mL and most preferably about 10 mg/mL;

maintaining an alkaline (basic) pH, e.g., in a range of 7 to 13, preferably 9 to 12, more preferably 10 to 11, and most preferably about 10.3 to 11, for a duration of about 24 hours, preferably less than 12 hours, more preferably less than 1 hour and most preferably about 10-30 minutes;

maintaining an acidic pH, e.g., a pH in a range of 1 to 6.9, preferably 2 to 5, more preferably 2.5 to 3.5, and most preferably about 3, for a duration of about 24 hours, preferably less than 12 hours, more preferably less than 1 hour and most preferably about 5-15 minutes;

neutralizing the solution to a pH between 4 and 8, preferably the solution is neutralized to a pH between 5 and 8, and more preferably to a pH between 6 and 8, and most preferably to a pH between 6 and 7;

precipitating and washing the modified pectin with ethanol;

dissolving the washed precipitate in water;

filtering the solution, preferably by microfiltration, e.g., through a 0.2 μm filter, such that the modified pectin passes through the filter; and concentrating and diafiltering the solution of modified pectin using ultrafiltration (e.g., using a 30 kD membrane).

In various embodiments, the processes outlined include sterile filtration, sterile filling, removal of endotoxins, lyophilization, or a combination of any of these.

The present invention contemplates several different types of modified pectin compositions with different attributes and potential uses. In one composition of the invention, the modified pectin is in a solution having a modified pectin concentration of at least 0.1 mg/mL, preferably at least 1 mg/mL, more preferably at least 5 mg/mL, at least 7 mg/mL, at least 10 mg/mL, or even at least 15 mg/mL. In certain embodiments, the solution is a 10-30% aqueous ethanol solution. In certain other embodiments, the modified pectin solution is substantially free of ethanol and acetone. In yet another preferred embodiment, the modified pectin composition described above has no ethanol or other organic solvent, such as acetone, ether, dimethylsulfoxide, ethyl acetate, etc.

In one embodiment, the invention provides a modified pectin comprising rhamnogalacturonan and/or homogalacturonan backbone with neutral sugar side chains, and having a low degree of neutral sugar branching dependent from the backbone. In certain embodiments, the modified pectin is deesterified and partially depolymerized, so as to have a disrupted rhamnogalacturonan backbone.

In one embodiment, the modified pectin includes a copolymer of galacturonic acid and rhamnogalacturonan I in which at least some of the galactose- and arabinose-containing sidechains are still attached. In preferred embodiments, the modified pectin has an average molecular weight of 50-200 kD, preferably 70-200 kD, more preferably 70-150 kD as measured by Gel Permeation Chromatography (GPC) with Multi Angle Laser Light Scattering (MALLS) detection.

In certain embodiments, the compositions are suitable for parenteral administration to a mammal, most preferably by injection or intravenous infusion. The composition may be adapted for direct injection or intravenous infusion, or for addition to an intravenous drip solution for gradual infusion, through appropriate use of excipients and packaging and delivery means well known in the art. In certain embodiments the compositions comprise one or more pharmaceutically acceptable excipients, such as water, pharmaceutically acceptable buffers, stabilizers, local anesthetics, and the like, as described in greater detail below.

In another aspect, the invention provides a pharmaceutical package, comprising a vial or ampoule containing a modified pectin according to the invention in the form of a reconstitutable powder or a solution suitable for injection or infusion, e.g., together with instructions for administering the composition to a patient in need thereof. Instructions include but are not limited to written and/or pictorial descriptions of: the active ingredient, directions for diluting the composition to a concentration suitable for administration, suitable indications, suitable dosage regimens, contraindications, drug interactions, and any adverse side-effects noted in the course of clinical trials.

The invention also provides a method for conducting a medical assistance reimbursement program, the method comprising: (a) providing a reimbursement program that permits, for prescription of a composition, solution, or depolymerized pectin of the invention for treating a cancer, at least partial reimbursement to a healthcare provider or patient, or payment to a drug distributor; (b) processing one or more claims for reimbursement of the cost of a prescription of the composition, solution, or depolymerized pectin for treating a cancer; and (c) reimbursing the healthcare provider or patient, or paying a drug distributor, at least a portion of the cost of said prescription.

In certain embodiments, a solution of modified pectin as described above is lyophilized, e.g., by methods well-known in the art, to provide a dry solid formulation adapted for reconstitution into a solution suitable for intravenous administration. Such lyophilized compositions may optionally comprise additives, such as wetting agents and sugars, to promote dissolution.

In certain embodiments, the invention provides a process for dissolving dry pectin in water at the beginning of the modification process. The process of dissolving the pectin in water is not straightforward, due to the unusual properties of dry hydrocolloid powders. Upon contact with water, the pectin particles rapidly swell and become sticky, and they tend to crowd against and adhere to any neighboring particles. The result is a sticky mass that dissolves very slowly, due to the limited surface area in contact with the water. It is preferable to keep the particles separated from one another long enough for them to disperse into the water, where the individual particles remain separated and can dissolve much more quickly.

Methods for separating pectin particles at the time of their dispersion in water include, but are not limited to, (a) use of an eductor funnel, (b) addition of a sugar, (c) suspension in a non-solvent, (d) use of high shear, and (e) slow, controlled addition of reagents. In a powder eductor funnel, the pectin particles are separated by a stream of air just before they contact the water. When a dry blend of several parts sugar to one part pectin is dispersed into water, the sugar particles separate the pectin particles, allowing the pectin particles to hydrate and expand without contacting their neighbors. Suspension in a non-solvent, such as vegetable oil, glycerin, ethanol, or corn syrup, results in the pectin particles becoming wetted and separated from one another without swelling or becoming sticky. The suspension is then be added to water with agitation. With the use of high shear, rapidly-moving water separates adhering particles and breaks up any lumps, maintaining a high surface area and enabling quick hydration. In the case of slow controlled addition, pectin may simply be added at a slow controlled rate to a stirring solution of water. Preferably, the rate of addition is sufficiently slow and the mixing speed is sufficiently great to allow the pectin to be rapidly dispersed and hydrated. Controlled pectin addition can be accomplished manually or with the use of a powder addition device, such as an automated solids metering device outfitted with an adjustable rate extruding screw.

In certain embodiments, modified pectins of the invention are described by either or both of formulas I and II below, and it is to be understood that variants of these general formulae may be prepared and utilized in accord with the principles of the present invention.

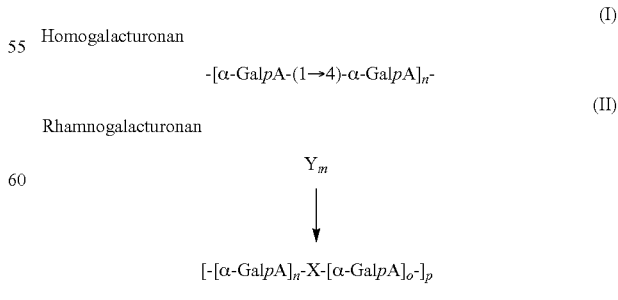

In the formulae above, m is $\geq 0$, n, o and p are $\geq 1$, X is α-Rha$p$; and $Y_m$ represents a linear or branched chain of sugars (each Y in the chain $Y_m$ can independently represent a different sugar within the chain). The sugar Y may be, but is not limited to, any of the following: α-Galp, β-Galp, β-Apif, β-Rhap, α-Rhap, α-Fucp, β-GlcpA, α-GalpA, β-GalpA, β-DhapA, Kdop, β-Acef, α-Araf, 13-Araf, and α-Xylp.

It will be understood that natural pectin does not possess a strictly regular repeating structure, and that additional random variations are likely to be introduced by partial hydrolysis of the pectin, so that the identity of $Y_m$ and the values of n and may vary from one iteration to the next of the p repeating units represented by formula II above.

Abbreviated sugar monomer names used herein are defined as follows: GalA: galacturonic acid; Rha: rhamnose; Gal: galactose; Api: erythro-apiose; Fuc: fucose; GlcA: glucuronic acid; DhaA: 3-deoxy-D-lyxo-heptulosaric acid; Kdo: 3-deoxy-D-manno-2-octulosonic acid; Ace: aceric acid (3-C-carboxy-5-deoxy-L-lyxose); Ara: arabinose. Italicized p indicates the pyranose form, and italicized f indicates a furanose ring.

II. Definitions

The term "healthcare providers" refers to individuals or organizations that provide healthcare services to a person, community, etc. Examples of "healthcare providers" include but are not limited to doctors, hospitals, continuing care retirement communities, skilled nursing facilities, sub-acute care facilities, clinics, multispecialty clinics, freestanding ambulatory centers, home health agencies, and HMO's.

A "patient" or "subject" to be treated by a method of the invention can mean either a human or non-human subject.

The term "$IC_{50}$" means the concentration of an agent that produces a 50% reduction in the effect compared to when there is a complete absence of the agent being tested for $IC_{50}$.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" as used herein means a pharmaceutically acceptable material, composition or vehicle, such as a liquid or solid filler, diluent, lubricant, binder, carrier, humectant, disintegrant, solvent or encapsulating material, that one skilled in the art would consider suitable for rendering a pharmaceutical formulation suitable for administration to a subject. Each excipient must be "acceptable" in the sense of being compatible with the other ingredients of the formulation, as well as "pharmaceutically acceptable" as defined above. Examples of materials which can serve as pharmaceutically acceptable excipients include but are not limited to: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; silica, waxes; oils, such as corn oil and sesame oil; glycols, such as propylene glycol and glycerin; polyols, such as sorbitol, mannitol and polyethylene glycol; esters, such as ethyl oleate and ethyl laurate; agar; buffering agents; alginic acid; pyrogen-free water; isotonic saline; Ringer's solution; and other non-toxic compatible substances routinely employed in pharmaceutical formulations.

By "substantially free" of ethanol or another solvent, it is meant that the compositions of the invention contain less than 5% of that solvent by weight. In preferred embodiments, the subject compositions contain less than 2%, less than 1%, and more preferably less than 0.5% ethanol by weight, and preferably less than 1% or 0.5% acetone by weight.

By "substantially free" of modified pectins having a certain molecular weight below a certain number, it is meant that the composition has less than 1%, preferably less than 0.5% or even less than 0.1%, of modified pectins having a molecular weight below that number.

A "therapeutically effective amount" of a compound, such as a modified pectin of the present invention, with respect to the subject method of treatment, refers to an amount of the compound(s) in a preparation which, when administered as part of a desired dosage regimen to a subject, slows or arrests the progress of the disease or condition sought to be treated.

III. Methods for Preparing Modified Pectins

A. Choice of Pectin Starting Material

Pectin is a major constituent of plant cell walls, and is a combination of at least three principal pectic polysaccharides, which are believed to be covalently linked within the cell wall: homogalacturonan (HG), rhamnogalacturonan I (RG-I), and rhamnogalacturonan II (RG-II).

HG is a linear homopolymer of 1,4-linked α-D-galacturonic acid, methyl esterified to varying degrees at C-6. Depending on the species of plant, the backbone galacturonic acid units may be C-3 substituted with O-acetyl residues.

RG-I is a heterologous group of polysaccharides that contain a backbone of the repeating disaccharide [→4)-α-D-GalpA-(1→2)-α-L-Rhap-(1→]. Between 20 and 80% of the Rhap residues are substituted at C-4 with neutral oligosaccharide side chains containing linear and branched α-L-Araf and β-D-Galp residues. The backbone GalpA residues of RG-I are not typically substituted with polysaccharides, although they may be O-acetylated at C2 or C3.

RG-II has a more highly conserved structure, with a backbone usually composed of at least seven to nine 1,4-linked a-D-GalpA residues, to which four complex oligosaccharide side chains are typically attached at C-2 and/or C-3.

Pectin itself is thought to be a heteropolysaccharide with a backbone composed of alternating HG ("smooth regions") and RG ("hairy regions"). The smooth regions are linear polymers of 1,4-linked α-D-galacturonic acid.

The highly branched "hairy regions" feature neutral sugar units (typically D-galactose or L-arabinose or xylose attached by glycosidic linkages to the C4 atoms of the rhamnose units, and/or to the C2 or C3 atoms of the galacturonic acid units. Depending upon the extraction process used, the hairy regions are partially or largely degraded during the manufacture of commercial pectin, leaving intact the smooth polygalacturonic acid regions, with a smaller number of neutral sugar units still attached to or embedded in the main linear chain. The methyl galacturonate ester groups survive the extraction process, although degree of methyl esterification may be reduced in subsequent processing steps to provide commercial pectins having various utilities.

The degree of methyl esterification in most commercial pectins varies from 0-90%. If 50% or more of the carboxyl groups are esterified the pectin is referred to as a "high ester" or "high methoxyl" pectin". If less than 50% of the carboxyl groups are esterified then the pectin is referred to as a "low ester" or "low methoxyl" pectin. Pectin having few or no esterified groups is referred to as pectic acid.

The choice of the starting pectin material affects the characteristics of the final product. However, in choosing a starting pectin, important things to consider are molecular weight, degree of esterification, monosaccharide content, linkage, polydispersity and so forth. In a preferred embodiment, the starting pectin contains roughly 50-60 mole % esterification or higher, has a molecular weight of greater than 150 kD, and has a particular monosaccharide content, e.g., galactose content, greater than or equal to 5%. In one embodiment of the invention the starting pectin composition may comprise approximately equal amounts of HG and RG-I, preferably at least 70% HG and less than 30% RG-I more preferably at least 80% HG and less than 20% RG-I and most preferably at least 90% HG and less than 10% RG-I. In certain embodiments, the pectin may contain 0-10% of RG-II. In certain preferred embodiments, the starting pectin is citrus pectin.

B. Structural Modification of Pectin

According to the invention, the term "modified pectin" herein refers to any changes to the structure of pectin that are brought about by chemical, physical or biological means or by some combination thereof. Non-limiting examples of changes to the pectin structure include (but are not limited to) deesterification, hydrolysis, oxidation and/or reduction of sugar moieties, functionalization of sugar moieties, conformational changes, and changes in molecular weight, linkage, states of aggregation, and particle size.

In one embodiment, modified pectin has the structure of a pectic acid polymer with some of the pectic side chains still present. In preferred embodiments, the modified pectin is a copolymer of homogalacturonic acid and rhamnogalacturonan I in which some of the galactose- and arabinose-containing sidechains are still attached. The modified pectin may have a molecular weight of 1 to 500 kilodaltons (kD), preferably 10 to 250 kD, more preferably 50-200 kD, 70-175 kD, 70-150 kD, or 80-150 kD, or even 80 to 100 kD as measured by Gel Permeation Chromatography (GPC) with Multi Angle Laser Light Scattering (MALLS) detection.

Degree of esterification is another characteristic of modified pectins. In certain embodiments, the degree of esterification may be between 0 and 80%, between 10 and 60%, between 0 and 50%, or between 20 and 60%, such as 20-45%, or 30-40% esterification.

Saccharide content is another characteristic of modified pectins. In certain embodiments, the modified pectin is composed entirely of a single type of saccharide subunit. In other embodiments, the modified pectin comprises at least two, preferably at least three, and most preferably at least four types of saccharide subunits. For example, the modified pectin may be composed entirely of galacturonic acid subunits. Alternatively, the modified pectin may comprise a combination of galacturonic acid and rhamnose subunits. In yet another example, the modified pectin may comprise a combination of galacturonic acid, rhamnose, and galactose subunits. In yet another example, the modified pectin may comprise a combination of galacturonic acid, rhamnose, and arabinose subunits. In still yet another example, the modified pectin may comprise a combination of galacturonic acid, rhamnose, galactose, and arabinose subunits. In some embodiments, the galacturonic acid content of modified pectin is greater than 50%, preferably greater than 60% and most preferably greater than 80%. In some embodiments, the rhamnose content is less than 25%, preferably less than 15% and most preferably less than 10%; the galactose content is less than 50%, preferably less than 40% and most preferably less than 30%; and the arabinose content is less than 15%, preferably less than 10% and most preferably less than 5%. In certain embodiments, the modified pectin may contain other uronic acids, xylose, ribose, lyxose, glucose, allose, altrose, idose, talose, gluose, mannose, fructose, psicose, sorbose or talalose in addition to the saccharide units mentioned above.

Modified pectin suitable for use in the subject methods may also have any of a variety of linkages or a combination thereof. By linkages it is meant the sites at which the individual sugars in pectin are attached to one another. In some embodiments, the modified pectin comprises only a single type of linkage. In certain preferred embodiments, the modified pectin comprises at least two types of linkages, and most preferably at least 3 types of linkages. For example, the modified pectin may comprise only alpha-1,4 linked galacturonic acid subunits. Alternatively, the modified pectin may comprise alpha-1,4-linked galacturonic acid subunits and alpha-1,2-rhamnose subunits. In another example, the modified pectin may be composed of alpha-1,4-linked galacturonic acid subunits and alpha-1,2-rhamnose subunits linked through the 4 position to arabinose subunits. In another example, the modified pectin may comprise alpha-1,4-linked galacturonic acid subunits and alpha-1,2-rhamnose subunits linked through the 4 position to arabinose subunits with additional 3-linked arabinose subunits. In another example, the modified pectin may comprise alpha-1,4-linked galacturonic acid subunits and alpha-1,2-rhamnose subunits linked through the 4 position to arabinose subunits with additional 5-linked arabinose units. In another example, the modified pectin may comprise alpha-1,4-linked galacturonic acid subunits and alpha-1,2-rhamnose subunits linked through the 4 position to arabinose subunits with additional 3-linked and 5-linked arabinose subunits. In another example, the modified pectin may comprise alpha-1,4-linked galacturonic acid subunits and alpha-1,2-rhamnose subunits linked through the 4 position to arabinose subunits with additional 3-linked and 5-linked arabinose subunits with 3,5-linked arabinose branch points. In another example, the modified pectin may comprise alpha-1,4-linked galacturonic acid subunits and alpha-1,2-rhamnose subunits linked through the 4 position to galactose subunits. In another example, the modified pectin may comprise alpha-1,4-linked galacturonic acid subunits and alpha-1,2-rhamnose subunits linked through the 4 position to galactose subunits with additional 3-linked galactose subunits. In another example, the modified pectin may comprise alpha-1, 4-linked galacturonic acid subunits and alpha-1,2-rhamnose subunits linked through the 4 position to galactose subunits with additional 4-linked galactose subunits. In another example, the modified pectin may comprise alpha-1,4-linked galacturonic acid subunits and alpha-1,2-rhamnose subunits linked through the 4 position to galactose subunits with additional 3-linked galactose subunits with 3,6-linked branch points. In another example, the modified pectin may comprise alpha-1,4-linked galacturonic acid subunits and alpha-1,2-rhamnose subunits linked through the 4 position to galactose subunits with additional 4-linked galactose subunits with 4,6-linked branch points. In certain embodiments, the side chains of the modified pectin may comprise uronic acids, galacturonic acid, glucuronic acid, rhamnose, xylose, ribose, lyxose, glucose, allose, altrose, idose, talose, gluose, mannose, fructose, psicose, sorbose or talalose in addition to the saccharide units described above.

Modified pectin according to the invention may have one, all or some subcombination of the characteristics described above.

Modification by Chemical Methods

Modified pectin may be produced by chemical means. By chemical means it is meant to include any chemical reaction or process that disrupts or changes chemical bonding of the pectin structure. Chemical bonding includes any bonding which is readily known in the art. By way of example this may include covalent or ionic bonds. Chemical reactions include any reaction known in the art and include those that either directly or indirectly alter chemical bonds. By way of example only, chemical bonding may be disrupted or formed by catalysis, hydrolysis, substitution, elimination, reduction, oxidation, and radical reactions. In certain embodiments, modified pectin according to the invention is produced by a process that includes hydrolysis, which is preferably catalyzed, e.g., by an acidic or basic reagent or both.

In one preferred embodiment, an aqueous solution of pectin is modified by the action of alkaline conditions. Under these conditions, the original pectin structure may undergo several changes. Non-limiting examples include de-esterification of the methylated galacturonic acid residues, cleavage of the galacturonic acid backbone, cleavage of the branch points, as well as conformational changes, for example from random coil to rigid rod, or change in aggregation state.

In another preferred embodiment an aqueous pectin solution is modified by the action of acidic conditions. Under these conditions, the structure of pectin may undergo several changes. These changes include, but are not limited to, de-esterification, hydrolysis of the backbone, branch points or side chains, conformational changes, for example from rigid rod to random coil, and changes in aggregation state.

In yet another more preferred embodiment, an aqueous pectin solution is treated sequentially to alkaline conditions followed by acidic conditions or vice versa.

In another embodiment, pectin is modified by the addition of salts. In one embodiment divalent salts such as calcium or magnesium are used to increase the molecular weight of the modified pectin by ionic bonding. In another embodiment, high salt concentrations are used to cause conformational changes to the pectin structure by interrupting intramolecular ionic and hydrogen bonding.

In alternative embodiments, pectin is modified by oxidation. In one preferred embodiment the C-6 hydroxyls of the galactose side chains are oxidized to carboxylic acids using methods known in the art, for example selective primary alcohol oxidation in aqueous solution using 2,2,6,6-tetramethyl-1-piperidinyloxy free radical (TEMPO).

In an alternative embodiment, pectin my also be modified by the use of a reductant. For example, the methyl esters of the C-6 carboxyl group on the galacturonic acid can be reduced to hydroxyl groups using sodium borohydride.

Modification by Physical Methods

In another aspect of the invention pectin may be modified by physical means. Physical means are meant to include non-chemical or biological means that alter the structure of pectin. Such physical means might include, but are not limited to heat, cold, freeze/thaw, irradiation, shear, ultra-high shear, addition of cosolvents and other ionic disrupting compounds, and filtration. In one embodiment, the particle size polydisperisty of a colloidal solution of modified pectin is reduced by the use of microfiltration. Particularly, a solution of modified pectin may be filtered using tangential flow filtration comprising a particular membrane type and pore size. In another embodiment, a modified pectin solution may be combined with a second solvent such as ethanol to compress the particle size by reduction of hydration prior to filtration.

The choice of filter pore size and membrane type, the amount of cosolvent, the pH, and concentration depend on the degree of polydispersity desired. In preferred embodiments, the pore size utilized is less than 1.0 µm, preferably less than 0.65 µm, more preferably less than 0.45 µm, and most preferably less than 0.22 p.m. In other preferred embodiments, ethanol is the cosolvent and is present at a concentration of less 0 to 40% w/w, more preferably 10 to 30% w/w, and most preferably 15-25% w/w. In a preferred embodiment, a pectin solution or a chemically modified pectin solution is filtered at a concentration of 2.5 to 7.5 mg/mL in 10 to 25% aqueous ethanol.

Modification by Biological Methods

In yet another aspect of the invention, pectin may be modified by biological means. Biological means are meant to include by way of example, enzymatic degradation of pectin. For example, a pectinase enzyme or cocktail of enzymes may be used to reduce the molecular weight of pectin. The choice of the enzyme(s) employed will depend upon the desired outcome. In one embodiment, the enzymes may be selected to hydrolyze the polygalacturonic backbone. In another embodiment, the enzyme(s) may be selected to hydrolyze the side chains from the backbone. In yet another embodiment, the enzyme or enzyme cocktail may be selected to alter the degree of esterification.

Modification by Alternative Methods

Finally, the invention contemplates the preparation of modified pectin by synthetic and/or recombinant methods. Like the production of recombinant proteins, complex polysaccharides might be engineered via a series of synthetic reactions or by recombinant methods.

In certain embodiments, the method of the invention includes any subcombination of the foregoing acts.

C. Methods of Controlling Therapeutic Effectiveness

The therapeutic effectiveness of modified pectin can be controlled by several methods including controlling molecular weight and particle size polydispersity, the degree of esterification, the average molecular weight, the pH, and the charge density. In one embodiment, the therapeutic effectiveness of a modified pectin is increased by reducing the particle size polydispersity by means of microfiltration. In a preferred embodiment, the microfiltration is tangential flow filtration. The degree of therapeutic effectiveness can be increased or decreased based upon the filtration conditions utilized. In particular, the filtration feed and filtration parameters can be adjusted to control the degree of therapeutic activity of the modified pectin. In general, the therapeutic activity of a modified pectin can be increased by one or a combination of the following parameters: adjusting the filtration feed to a lower pH prior to filtration, increasing the concentration of the modified pectin in the filtration feed, adding a cosolvent such as ethanol or increasing the ratio of filtration membrane surface area to weight of filtered product. The invention contemplates that additional parameters or other means can be employed to achieve the same result. For example, ultrasonication or high shear methods may also be employed to create smaller particle sizes.

Methods of Controlling Molecular Weight

The molecular weight of modified pectin may also be controlled, e.g., increased or decreased. Increases in molecular weight may be brought about by formation of ionic interactions, hydrogen bonds, covalent bonds, or some combination thereof.

Decreases in molecular weight may be brought about by interruption of ionic interactions, hydrogen bonds, or covalent bonds, e.g., by acid-catalysed hydrolysis, base-catalyzed cleavage, or some combination thereof. In one embodiment of the invention, the molecular weight of pectin or modified pectin is reduced by hydrolysis of the covalent linkages of main backbone, hydrolytic removal of the side chains, or some combination thereof. In a specific example, the molecular weight is reduced by increasing the pH of an aqueous solution of pectin. The rate of the hydrolysis is controlled by pH and time. In one method, the pH of the solution is between 7-13. In a preferred method, the pH of the solution is between 8.5-11.5, more preferably between 10-11.

In certain embodiments, the molecular weight is reduced by increasing the temperature of either dry pectin, solutions of pectin, or suspensions of pectin. The rate of decrease in molecular weight is controlled by temperature and time. In one method the temperature is between 50 and 200° C., more preferably between 80 and 150° C. and most preferably between 95 and 125° C. When decreasing the molecular weight using heat, the type of vessel used may affect the rate of the reaction. For example, when heating a solution it may be optimal to conduct the heating in a closed vessel. This closed system will not allow loss of volume, but must be able to withstand the vapor pressure generated by the reaction. Additionally, the presence of oxygen (either dissolved or atmospheric) may cause unwanted side reactions, such as oxidation. This can be avoided by running the reaction in a closed vessel under vacuum or purged with nitrogen, or by other methods known in the art.

In certain embodiments, molecular weight may be affected by irradiation. High-energy radiation such as gamma irradiation is known to cause the scission or formation of new bonds through the formation of radicals. The degree of molecular weight modification is dependent on several variables such as intensity of the irradiation, exposure duration, dissolved or atmospheric oxygen, and density of material being irradiated. However, in one method, an aqueous solution of pectin in a closed vessel under vacuum is irradiated for at least 1 minute, preferably at least 10 minutes, more preferably at least 30 minutes and most preferably at least 60 minutes and the intensity of the irradiation is at least 1 kilogray, preferably at least 5 kilogray, more preferably 15 kilogray, and most preferably 25 or more kilogray.

In certain embodiments, the molecular weight may reduced by shear. Shear may be produced by a number of methods which are known in the art, and may include sonication and high shear mixing.

In certain embodiments, the molecular weight of a modified pectin may be increased by the action of a chemical crosslinker. In one embodiment, the molecular weight of modified pectin is increased by crosslinking it with a water soluble diamine, such as poly(ethyleneglycol)bisamine using a carbodiimide intermediate.

Depending on the final product desired, the above methods for modulating the molecular weight may be performed individually or in some combination.

Methods For Controlling Molecular Weight Polydispersity

In some instances it may be desirable to optimize the final polydispersity of the modified pectin. For example, modified pectins of a particularly narrow molecular weight range or colloidal particle size may give optimal pharmaceutical performance.

The polydispersity of modified pectin can be controlled by the mechanical removal of products having unwanted molecular weights. In certain embodiments, the unwanted products are eliminated by one or more fractional precipitations. In certain preferred embodiments, unwanted products are removed by either one or a series of ultrafiltrations with differing nominal molecular weight cut-off membranes. Ultrafiltration is a well known process and typically takes place in an aqueous solvent.

The polydispersity can be reduced by using size exclusion chromatography. In this method, a modified pectin solution is passed through a size exclusion column which differentially separates molecules based on their molecular weight.

The polydispersity of the modified pectin can be controlled by its method of manufacture. In one such method, the polydispersity of the pectin or modified pectin is decreased by exposing a solution or suspension to ultrahigh shear. The action of shear, especially ultrahigh shear, causes bonds of larger polymers to break preferentially at about the middle of the polymer, leaving smaller polymers intact. This action will result in the preferential formation of smaller polymers of approximately the same size and thus a smaller polydispersity.

Methods for Controlling Monosaccharide Content

There are a wide variety of enzymes, including some produced by bacteria and fungi, that selectively fragment particular segments of the pectin polysaccharide. Various combinations of these enzymes may be employed to remove methyl esters, individual sugars, side chains, or sections of the backbone as desired. Enzymes that can be used alone or in combination to alter monosaccharide composition include, for example, rhamnogalacturonase, rhamnogalacturonan lyase, rhamnogalacturonan-rhamnohydrolase, rhamnogalacturonan-galacturonohydrolase, endo and exo galacturonases, arabinases, pectin methyl esterases, and galactanases.

The monsaccharide content of modified pectin can be controlled by the conversion of one type of monosaccharide moiety into another. In one embodiment of the invention, the galacturonic acid content of the modified pectin is reduced by the selective chemical reduction of the carboxyl on C-6 of galacturonic acid to form galactose. The monosaccharide content can also be affected by the source of the pectin starting material, as discussed above.

Methods for Controlling Linkage

Linkages can be controlled by choice of the source of the starting pectin, the nature of the chemical process to produce the modified pectin, and enzymatically by selective cleavage with enzymes. In one embodiment, acid hydrolysis is used to preferentially cleave the neutral side chains from the pectin backbone.

D. Methods of Purification

Typically, the processes of making modified pectin result in a mixture of modified pectin and a number of impurities such as low molecular weight by-products, salts, co-solvents and inactive modified pectin. In certain embodiments of the invention, these impurities are acceptable and modified pectin is not further purified or isolated. In other more preferred embodiments, the impurities are either reduced or removed entirely from the modified pectin composition.

According to the invention, impurities can be removed by methods known in the art. By way of example, these methods include filtration, microfiltration, ultrafiltration, chromatography, centrifugation, extraction, drying, precipitation and dialysis.

Impurities may be separated from modified pectin by screen filtration, microfiltration, ultrafiltration, or a combination thereof. For example, microfiltration of an aqueous modified pectin solution can be used to remove insoluble materials from the solution, while salts and low molecular weight by-products can be removed by using ultrafiltration. The choice of the membrane and its nominal molecular weight cut-off depends on the molecular size of the impurities which are to be removed and the molecular weight of the modified pectin product desired. In certain embodiments, a solution of modified pectin is purified by screen filtration using a 5 μm filter screen, by microfiltration through a 0.2 μm filter, by ultrafiltration through a 30 kilodalton ultra-filter, or any combination of these.

Modified pectin may also be purified by chromatography. The type of chromatography is selected based on the nature of the impurities to be removed; methods for choosing a suitable type of chromatography are well known in the art. Exemplary types of chromatography include size exclusion, ion exchange, and affinity chromatography.

Solvents, such as ethanol, acetone, water, etc., can be removed by any means known in the art, such as by drying or evaporation. In certain embodiments, solvents may be removed by lyophilization or vacuum distillation.

E. Methods of Formulating Modified Pectin Compositions

Any or all of the above methods may be combined to formulate modified pectin compositions suitable for therapeutic uses.

In certain embodiments, preparing modified pectin comprises partially depolymerizing a pectin polymer by disrupting the rhamnogalacturonan backbone, deesterifying galacturonic acid moieties in the backbone, and breaking down side chains of neutral sugars. In certain embodiments, the method preferably generates a substantially ethanol-free product suitable for parenteral administration.

In one exemplary method of the invention, preparing modified pectin compositions comprises:

dissolving the pectin in water at a concentration of 0.1 to 40 mg/mL, preferably 1 to 20 mg/mL, more preferably 5 to 15 mg/mL and most preferably about 10 mg/mL;

depolymerizing and de-esterifying the pectin by digestion, e.g., at an alkaline pH of 7 to 13, preferably 9 to 12, more preferably 10 to 11, and most preferably about 10.7, for a duration of less than about 24 hours, preferably less than 12 hours, more preferably less than 1 hour, and most preferably about 10-30 minutes;

further digesting the pectin at an acidic pH from 1 to 6.9, preferably 2 to 5, more preferably from 2.5 to 3.5, and most preferably about 3, for a duration of several days, preferably about 24 hours, preferably less than 12 hours, more preferably less than 1 hour, and most preferably about 5-15 minutes;

neutralizing or adjusting the solution to a pH from 4 to 8, preferably from to 8, more preferably from 6 to 8, and most preferably from 6 to 7;

precipitating and washing the modified pectin with ethanol;

dissolving the washed precipitate in water;

filtering the solution through a filter, e.g. a 0.2 μm filter; and concentrating and diafiltering the solution of modified pectin by ultrafiltration using, e.g., a 30 kD-molecular weight cut-off membrane.

In certain embodiments, the method further includes adjusting the solution to isoosmolality and/or clarifying the solution. In certain embodiments, the method further includes fractionating the modified pectin molecules by size. Sizing can include fractionation of different particle sizes, molecular weight, particle or molecular shape. The method may further include sterile filtration, addition of sterile filling, removal of endotoxins, lyophilization, or any combination of these steps. Preferably, all of these additional steps are performed.

In certain embodiments of the above described method, dissolving the pectin comprises providing a slurry of pectin in a water-miscible organic solvent and combining the slurry with water to dissolve the pectin. The use of a slurry of pectin in a water-miscible organic solvent accelerates the dissolution and/or prevents the aerial dispersion of pectin particles that occurs when dry pectin is added directly to an aqueous solvent. The organic solvent preferably is or contains an alcohol, and more preferably the solvent is ethanol.

The alkaline pH as described above may be obtained by addition of an alkaline salt or a solution thereof, or in an alternative embodiment the water used to dissolve the pectin may already contain a dissolved alkaline salt and have a pH in the desired range. Suitable alkaline salts include but are not limited to sodium hydroxide, sodium carbonate, potassium hydroxide, and potassium carbonate. Preferably, sodium hydroxide is employed.

The acidic pH as described above may be achieved by addition of an acid, preferably a mineral acid or solution thereof. Examples of suitable mineral acids include but are not limited to hydrochloric acid, sulfuric acid, and acid salts such as sodium bisulfate and monobasic sodium phosphate.

The neutralization process as described above involves the addition of an alkaline salt or a solution of an alkaline salt, as described above. Optionally, a buffer such as a phosphate or carboxylate salt may be introduced as an aid to the neutralization process, for example to minimize local extremes in pH.

In certain embodiments, filtration of the dissolved precipitate as described above is carried out using tangential flow filtration. The effect of the filtration on the modified pectin can be influenced by the make-up of the feed solution (such as modified pectin concentration, cosolvent concentration, pH, conductivity, and temperature) and the filtration operating parameters utilized (transmembrane flow rate, filter surface area, and retentate flow rate). In one preferred embodiment, the modified pectin is filtered using a 0.2 μm tangential flow filter.

In preferred embodiments, preparing modified pectin comprises ultrafiltration of the solution of modified pectin (e.g., using a 30 kD membrane) as described above.

IV. Delivery of Modified Pectin

In certain embodiments, the compositions are suitable for parenteral administration to a mammal, most preferably by injection or intravenous infusion, and in some embodiments the compositions may comprise one or more pharmaceutically acceptable excipients. Suitable excipients include pharmaceutically acceptable buffers, stabilizers, local anesthetics, and the like. The composition may be adapted for direct injection or intravenous infusion, or for addition to an intravenous drip solution for gradual infusion, through appropriate use of excipients and packaging and delivery means well known in the art.

In another aspect, the invention provides a pharmaceutical package, comprising a vial or ampoule containing a modified pectin according to the invention in the form of a reconstitutable powder or a solution suitable for injection or infusion, together with instructions for administering the composition to a patient in need thereof. Instructions include but are not limited to written and/or pictorial descriptions of: the active ingredient, directions for diluting the composition to a concentration suitable for administration, suitable indications, suitable dosage regimens, contraindications, drug interactions, and any adverse side-effects noted in the course of clinical trials.

In an alternative embodiment of the above aspect of the invention, the pharmaceutical package may comprise a plastic bag containing from 100 ml to 2 L of a pharmaceutical composition of the invention, in the form of a solution suitable for intravenous administration, together with instructions as described above.

In alternative embodiments, a pharmaceutical composition of the invention may be in a form adapted for oral dosage, such as for example a syrup or palatable solution; a form adapted for topical application, such as for example a cream or ointment; or a form adapted for administration by inhalation, such as for example a microcrystalline powder or a solution suitable for nebulization. Methods and means for formulating pharmaceutical ingredients for alternative routes of administration are well-known in the art, and it is to be expected that those skilled in the relevant arts can adapt these known methods to the modified pectins of the invention.

The present invention provides pharmaceutically acceptable compositions comprising a therapeutically effective amount of one or more of the modified pectins of the invention, formulated together with one or more pharmaceutically acceptable excipients. The pharmaceutical compositions of the present invention may be formulated for administration in solid or liquid form, including forms adapted for oral administration, for example, aqueous or non-aqueous solutions or suspensions, tablets, powders, and granules; administration by inhalation, for example, aerosols, solutions for nebulization, or dry powders; parenteral administration, for example sterile solutions or suspensions; topical application, for example lotions, creams, ointments or sprays; ophthalmic administration; or intravaginal or intrarectal administration, for example pessaries, suppositories, creams or foams. Preferably, the pharmaceutical preparation is adapted for parenteral administration, more preferably it is a non-pyrogenic solution adapted for intravenous administration.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention may optionally be scored or prepared with coatings and shells, such as enteric coatings and other coatings well known in the pharmaceutical-formulating art. They may also be formulated so as to provide slow or controlled release of the modified therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally in a delayed manner. Examples of embedding compositions that can be used include polymeric substances and waxes. The modified pectin can also be in micro-encapsulated form, if appropriate, with one or more of the above-described excipients.

Liquid dosage forms for oral administration of the modified pectins of the invention include pharmaceutically acceptable emulsions, microemulsions, solutions, suspensions, syrups and elixirs. In addition to the modified pectin, the liquid dosage forms may contain inert diluents commonly used in the art, such as, for example, water or other solvents, solubilizing agents and emulsifiers.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In dry powder formulations adapted for inhalation, the particle size of the particulate medicament should be such as to permit inhalation of substantially all of the medicament into the lungs upon administration of the aerosol formulation and will thus desirably be less than 20 microns, preferably in the range 1 to 10 microns, more preferably 1 to 5 microns. The particle size of the medicament may be reduced by conventional means, for example by milling or micronisation. The aerosol formulation preferably contains 0.5-30% w/w of modified pectin relative to the total weight of the formulation.

The propellant may optionally contain an adjuvant having a higher polarity and/or a higher boiling point than the propellant. Polar adjuvants which may be used include (e.g. $C_{2-6}$) aliphatic alcohols and polyols such as ethanol, isopropanol and propylene glycol, preferably ethanol. In general only small quantities of polar adjuvants (e.g. 0.05-3.0% w/w) may be required to improve the stability of the dispersion. However, the formulations of the invention are preferably substantially free of polar adjuvants, especially ethanol. Suitable propellants include trichlorofluoromethane (propellant 11), dichlorodifluoromethane (propellant 12), dichlorotetrafluoroethane (propellant 114), tetrafluoroethane (propellant 134a) and 1,1-difluoroethane (propellant 152a), saturated hydrocarbons such as propane, n-butane, isobutane, pentane and isopentane, and alkyl ethers such as dimethyl ether. In general, up to 50% w/w of the propellant may comprise a volatile adjuvant, for example 1 to 30% w/w of a volatile saturated C1-C6 hydrocarbon.

The aerosol formulations according to the invention may optionally comprise one or more surfactants that are physiologically acceptable upon administration by inhalation.

For administration by inhalation, the drug is suitably inhaled from a nebulizer, from a pressurized metered dose inhaler or as a dry powder from a dry powder inhaler optionally using gelatin, plastic or other capsules, cartridges, blister packs and/or strips.

Administration of medicament may be indicated for the treatment of mild, moderate or severe acute or chronic symptoms or for prophylactic treatment. It will be appreciated that the precise dose administered will depend on the age and condition of the patient, the particular particulate medicament used and the frequency of administration and will ultimately be at the discretion of the attendant physician. Typically, administration will range from one or to four or more times daily.

For use in dry powder inhalers, the active ingredient can be modified by spray drying or compression to form a powder with suitable flow properties. More commonly a diluent or carrier is added which is generally non-toxic and inert to the medicament. Examples of such carriers are polysaccharides e.g. starch and cellulose, dextran, lactose, glucose, mannitol, and trehalose. The carrier can be further modified by the addition of surface modifiers, pretreatment to form low rugosity particles, addition of glidants, and flavor masking or modifying agents.

Pharmaceutical compositions of this invention suitable for parenteral administration comprise a modified pectin of the invention in combination with one or more pharmaceutically acceptable sterile isotonic aqueous or non-aqueous solutions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions.

Examples of pharmaceutically acceptable antioxidants include but are not limited to ascorbic acid, cysteine hydrochloride, sodium metabisulfite, sodium sulfite, ascorbyl palmitate, butylated hydroxyanisole (BHA), butylated hydroxytoluene (BHT), propyl gallate, alpha-tocopherol, and chelating agents such as citric acid, ethylenediamine tetraacetic acid (EDTA), sorbitol, tartaric acid, phosphoric acid, and the like.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

Dosage forms for the topical or transdermal administration of a compound of this invention include powders, sprays, ointments, pastes, creams, lotions, gels, solutions, patches and inhalants. The modified pectin may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Ophthalmic formulations, eye ointments, powders, solutions and the like, are also contemplated as being within the scope of this invention.

Formulations of the present invention which are suitable for vaginal administration include pessaries, tampons, creams, gels, pastes, foams or spray formulations, containing such carriers as are known in the art to be appropriate. Such formulations may be prepared, for example, by mixing one or more modified pectins of the invention with one or more suitable nonirritating excipients comprising, for example, cocoa butter, polyethylene glycol, or a suppository wax, which is solid at room temperature but liquid at body temperature and, therefore, will melt in the rectum or vaginal cavity and release the active modified pectin.

V. Uses of Modified Pectin

In another aspect, the invention provides a method of inhibiting a cell proliferation process in a patient, which comprises administering a pharmaceutical composition of the invention to the patient, thereby inhibiting the cell proliferation process. Cell proliferative processes include but are not limited to angiogenesis and cell proliferative disorders such as psoriasis, endometriosis, benign hyperplasias, and various types of cancer, including renal cell cancer, Kaposi's sarcoma, chronic leukemia, chronic lymphocytic leukemia, lymphoma, mesothelioma, breast cancer, sarcoma, myeloma, ovarian carcinoma, rectal cancer, throat cancer, melanoma, colon cancer, bladder cancer, mastocytoma, lung cancer, liver cancer, mammary adenocarcinoma, pharyngeal squamous cell carcinoma, prostate cancer, pancreatic cancer, gastrointestinal cancer, and stomach cancer.

In yet another aspect, the invention provides a method of enhancing the effects of conventional cancer treatments including chemotherapy, radiation therapy, surgery, and combinations thereof. Additionally, the invention provides treatments of other hyperproliferative disorders, diseases associated with corneal neovascularization, diseases associated with chronic inflammation, and autoimmune diseases. Further disclosure of related compositions and use are disclosed in U.S. Pat. No. 6,680,306 and U.S. patent application Ser. Nos. 08/024,487, 10/299,478, 10/176,022, and 60/461,006 the disclosures of which are incorporated herein by reference.

The invention also provides a method for conducting a medical assistance reimbursement program, the method comprising: (a) providing a reimbursement program that permits, for prescription of a composition, solution, or depolymerized pectin of the invention for treating a cancer or other disorder associated with cell proliferation, at least partial reimbursement to a healthcare provider or patient, or payment to a drug distributor; (b) processing one or more claims for reimbursement of the cost of a prescription of the composition, solution, or depolymerized pectin for treating a cancer; and (c) reimbursing the healthcare provider or patient, or paying a drug distributor, at least a portion of the cost of said prescription.

EXAMPLES

By way of example, and not limitation, the following examples are provided. Modified pectin materials were prepared as described herein, and the therapeutic affects of modified pectin were evaluated using two in vitro models, Cell Apoptosis Model, described in Example 4, and DNA Synthesis Inhibition Model, described in Example 5.

Example 1

Preparation of Modified Pectin

Citrus fruit pectin (800 g) was added (at a rate of about 15 g/min) with vigorous stirring to water (89 liters). Following addition of the pectin, the mixture was stirred for approximately 1 hour until the pectin appeared dissolved. The solution was then rapidly adjusted to pH 10.7 by the addition of ~10 N NaOH solution, and stirred at about 27° C.) for 20 minutes, while maintaining pH 10.7 using ~10 N NaOH. Following this the solution pH was adjusted to pH 3.0 by gradual addition of 3 M HCl and maintained for 10 minutes. The pH was then adjusted to 6.3 using 10 M and 1M NaOH and maintained for 10 minutes.

The resulting solution was then transferred into a 70% ethanol solution to precipitate the modified pectin. The precipitate was then isolated by screen filtration and washed with a 70% ethanol solution.

The precipitate was then dissolved in water, adjusted to 5 mg/mL modified pectin, 15% w/w ethanol and pH 6.5. The resulting solution was then filtered through a 0.2 µm tangential flow filter. This was followed by ultrafiltration and diafiltration through a 30 kD membrane to concentrate the modified pectin and reduce low molecular weight impurities including ethanol. The solution was then diluted with water to a final modified pectin concentration of 5 mg/mL.

This final solution was then filtered through 0.2 µm filters and filled into sterile glass vials. The modified pectin composition obtained by this process exhibited an ethanol content of less than 1%, an average molecular weight of approximately 90 kD as judged by a multiangle, light-scattering chromatography method, a modified pectin concentration of 5±0.5 mg/mL as determined by a size exclusion chromatography method. The composition was tested by the cancer Cell Apoptosis and DNA Synthesis Inhibition models described in Example 4 and 5, respectively, and found to be highly effective in both, with an average $IC_{50}$=50 µg/mL.

Example 2

Effect of Microfiltration Conditions on Therapeutic Effectiveness

The effect of varying microfiltration conditions on the control of therapeutic effectiveness was demonstrated by varying different filtration parameters and testing the modified pectin for activity in the cancer Cell Apoptosis model. Modified pectin was fractionated by size using microfiltration. FIG. 1 demonstrates that the samples prepared using different microfiltration pore sizes have different therapeutic effectiveness. In the range used in this experiment, the largest pore size (0.7 µm) had the least therapeutic effect while the smallest pore size (0.1 µm) had the most therapeutic effect, as determined by the Cell Apoptosis model.

Figure 2:
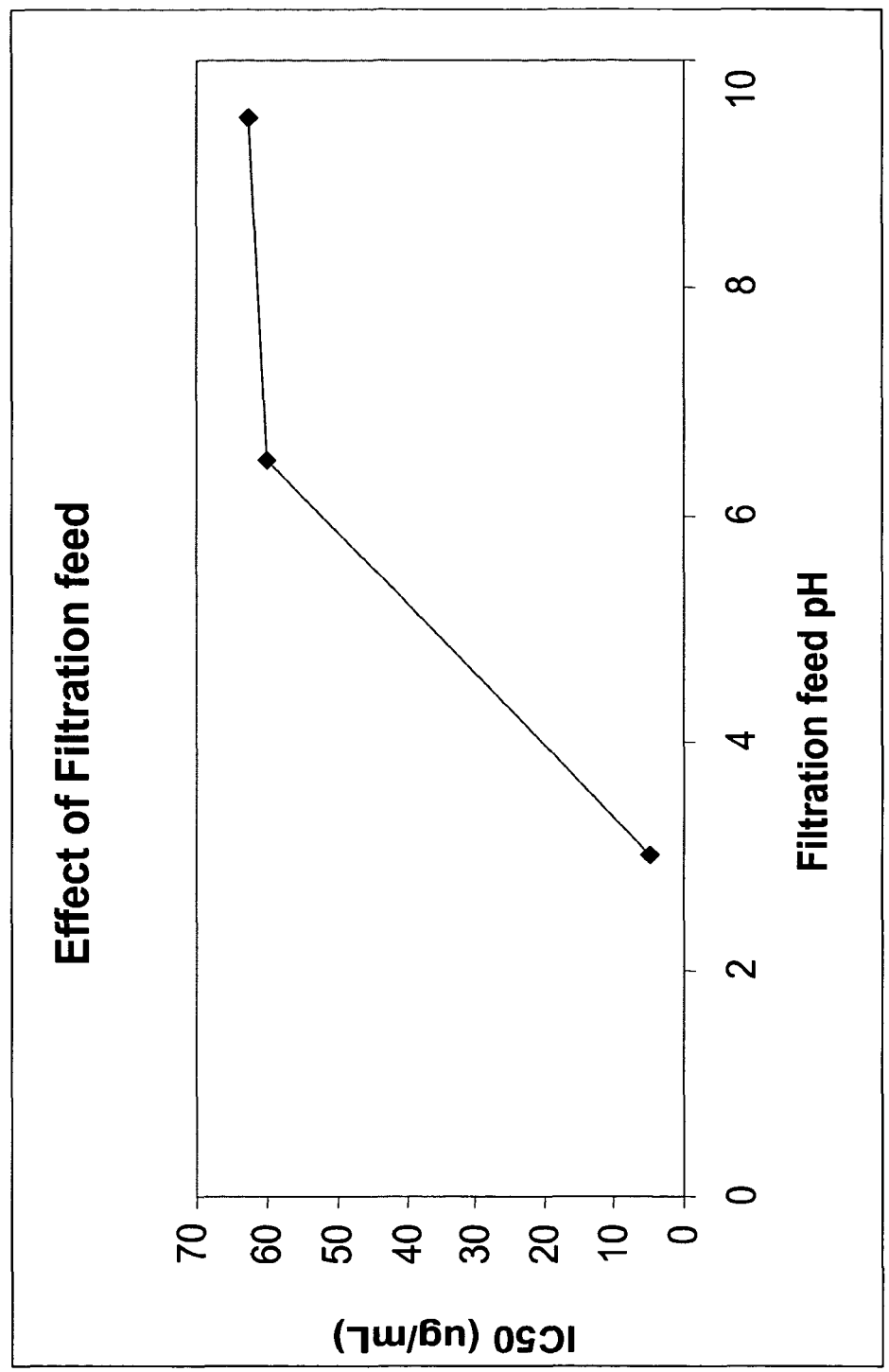
FIG. 2 demonstrates the effect of microfiltration feed pH on therapeutic effectiveness.

The pH of a sample that is filtered by the microfiltration procedure ("microfiltration feed") also has an effect on the therapeutic effectiveness of the prepared sample. FIG. 2 demonstrates the relationship between microfiltration feed pH and therapeutic effectiveness. In the range used in this experiment, the samples prepared from lower feed pH demonstrated higher therapeutic effect, as determined by the Cell Apoptosis model.

Figure 3:
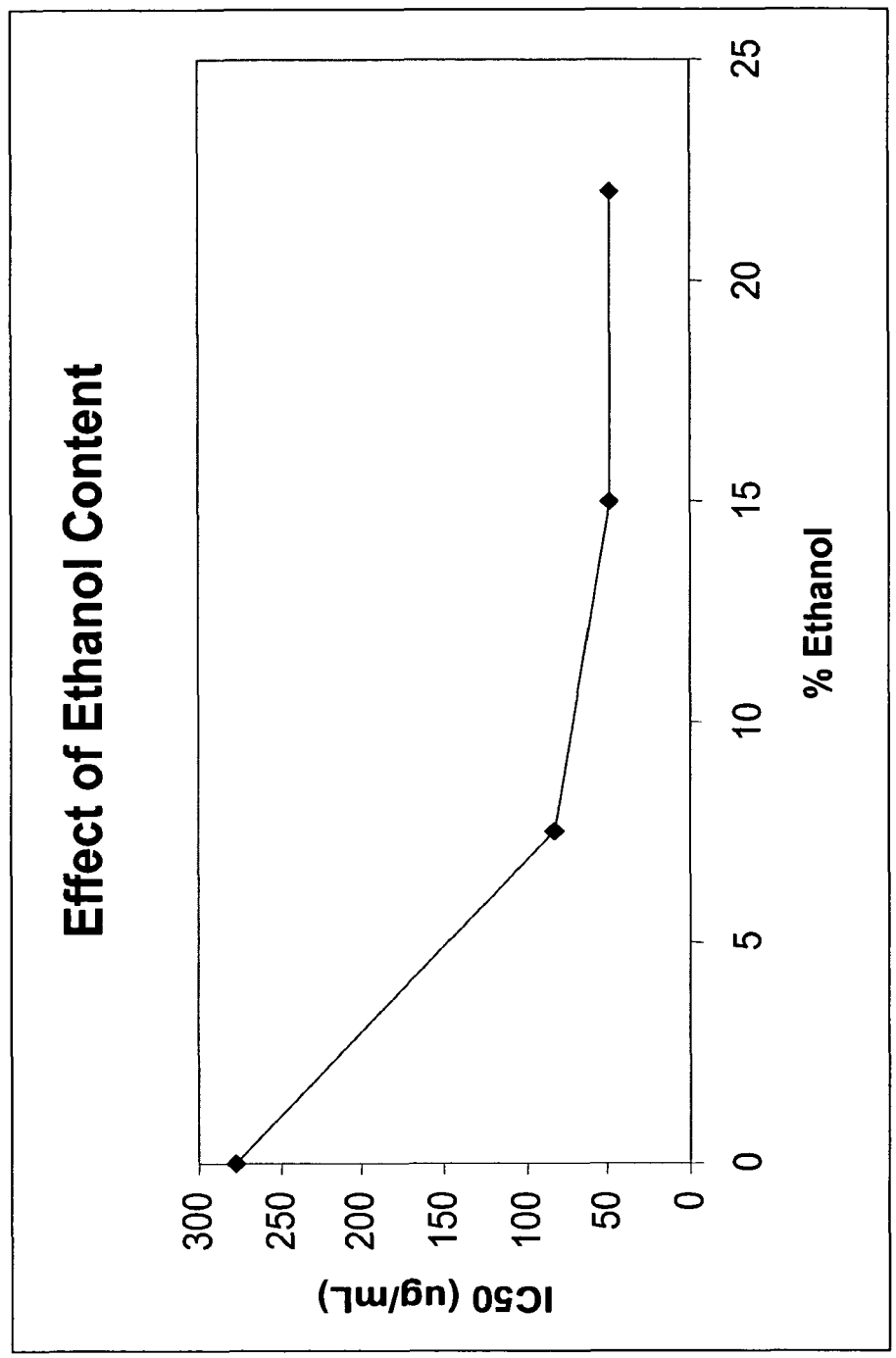
FIG. 3 demonstrates the effect of microfiltration feed ethanol content on therapeutic effectiveness.

Another factor that influences the therapeutic effectiveness of modified pectin is the ethanol content of the microfiltration feed. FIG. 3 demonstrates the effect of microfiltration feed ethanol content on therapeutic effectiveness. In the range used in this experiment, the samples processed with the higher ethanol concentrations demonstrated higher therapeutic effect, as determined by the Cell Apoptosis model.

For the three parameters tested, the modified pectin was prepared as described in Example 1, except the tangential flow filtration feed solution was modified appropriately.

Example 3

Modified Pectin Produced Via Physical Methods Only

As disclosed above, pectin can be modified by physical methods alone. This was demonstrated by preparing a pectin solution and processing by tangential flow filtration using filter feed conditions provided in the Example 1. The resulting material was tested for therapeutic activity in the cancer cell apoptosis model and it was found to have an $IC_{50}$ of 46 µg/mL whereas the unfiltered pectin feed solution had no detectable therapeutic activity.

Example 4

Cell Apoptosis Therapeutic Model

An experimental model to assess a potential anti-cancer agent is Cell Apoptosis Therapeutic Model. In this model, cancer cell apoptosis was demonstrated using an in vitro bioactivity assay. The test is qualitative and is based on the observation that modified pectin inhibits the proliferation of cancer cells such as B16-F10 mouse melanoma cells and induces cancer cell apoptosis. This effect can be measured by using a mitochondrial enzyme indicator such as AlamarBlue™ (BioSource), which is formulated to quantitatively measure the proliferation or viability of a variety of human or animal cells in the presence of adding toxic compounds. It consists of an oxidation-reduction (REDOX) indicator that yields a colorimetric change and a fluorescent signal in a response to the cell innate metabolic activity change, thereby providing an indirect measure of viable cell number. By testing several concentrations of the modified pectin, it is possible to calculate an $IC_{50}$ for the compound measured in µg/milliliter and the smaller the $IC_{50}$ the greater the therapeutic effect.

B16F10 cells were seeded into the wells of 96-well plates in growth media. After cells attached to the plates, 0, 5, 50, or 150 µl/ml of sterile 4-chlorodiazepam and 100 µl/ml of a sample to be tested were applied to the cells. The cells were incubated to allow viable cells to proliferate, and the media was replaced with fresh media supplemented with 10% AlamarBlue™. The cells were further incubated, then the state of oxidation of AlamarBlue™ was determined by spectrophotometry and adjusted for blanks. The more reduced AlamarBlue™ was, the higher the proportion of the cells that underwent apoptosis.

Example 5

DNA Synthesis Inhibition Therapeutic Model

The ability of the compound of the present invention to inhibit DNA synthesis was assessed by the BrdU assay. The BrdU assay measures de novo DNA synthesis as an indicator of cell proliferation. BrdU (5-bromo-2'-deoxy-uridine) is a nucleotide analogue that substitutes for thymidine during DNA synthesis in proliferating cells. Incorporated BrdU is proportional to the amount of newly synthesized DNA and can be detected by anti-BrdU monoclonal antibodies in ELISA, flow cytometry, or immunohistochemistry.

To compare the effects of modified citrus pectin (MCP) of the current invention to MCP generated by previously disclosed methods on cell proliferation, BrdU incorporation in B16-F10 mouse melanoma cells (ATCC, Manassas, Va.) was measured by Cell Proliferation ELISA, BrdU (Roche Applied Science, Indianapolis, Ind.). B16-F10 cells were grown in a 50:50 v/v media composed of EMEM and Leibovitz L-15 (both from Cambrex Bio Science, Walkersville, Md.) supplemented with 10% fetal bovine serum (JRH Bioscience, Lenexa Kans.), glutamine (JRH Bioscience), and penicillin-streptomycin (Invitrogen, Carlsbad, Calif.). Cells were seeded at 3,000/well in 96-well white-walled, clear bottom microtiter plates (Corning Life Sciences, Acton, Mass.) and grown for 24 h. The supernatant was removed and replaced with the MCP's dissolved in the supplemented 50:50 media. BrdU was added immediately following the agents. After 24 h agent and BrdU exposure, the cells were fixed and BrdU was detected with peroxidase-conjugated anti-BrdU. The luminescent signal was developed with luminol and hydrogen peroxide and measured with a HT Synergy plate reader (Bio-Tek Instruments, Winooski, Vt.).

Example 6

Demonstration of Improved Therapeutic Activity for Modified Pectin Prepared by Using the Methods of the Current Invention Versus Previous Methods The improved therapeutic activity of modified pectin using the methods disclosed in the current invention versus previously described methods was demonstrated by preparing material according to the method described in U.S. Application Publication No. US2002/0107222A1 and comparing it against material prepared using the methods described herein.

A first sample was prepared by the previous method described in US2002/0107222A1. Briefly, pectin was dissolved in water at a concentration of about 5 mg/mL. Using a 3 N sodium hydroxide (NaOH) solution, the pH was adjusted to 10 and maintained for 34 minutes. This was followed by acidification to pH 3 using 3 N NaOH. The solution was then incubated at room temperature (~17° C.) with stirring for 10 hours. The pH was then adjusted to pH 6.3 with 1 N NaOH. The resulting solution was then poured into a stirring solution of 70% w/w ethanol (2 parts 70% ethanol to 1 part solution) and left to precipitate for ~16 hours. The resulting precipitate was collected using vacuum filtration followed by washing with 70% ethanol. The collected precipitate was then dried by several suspensions in acetone followed by filtration. The resulting powder was then placed under vacuum for 10 hours to remove the residual solvent. A 5 mg/mL solution was prepared and labeled as JR017047-2.

A second sample was prepared using the methods described in Example 1, except the material collected and washed by screen filtration was then dried using several acetone suspensions and filtrations. The resulting powder was then dried under vacuum to remove the residual solvent. A 5 mg/mL solution was prepared and labeled JR017053-2.

A third sample was prepared using the methods described in Example 1 and labeled KB027002-9. Additionally, as a fourth sample, a sample of the tangential flow filtration feed solution was taken and labeled KB027002-8.

A fifth and six samples were prepared using the methods outlined in Example 1 and labeled 6612 and BB023013-10.

All of the above samples were tested by the Cell Apoptosis therapeutic model. In addition, all samples except the third and fourth samples were tested by the DNA Synthesis Inhibition therapeutic model.

Table 4 outlines the Cell Apoptosis therapeutic testing results from the six samples outlined above. As indicated, the materials produced using methods of the current invention (third, fifth, and sixth sample, labeled KB027002-9, BB023013-10, and 6612 respectively) exhibited greater therapeutic effectiveness compared to the formerly disclosed methods. Additionally, the data indicates this greater effectiveness is directly related to the content of the current invention, namely the inclusion of the additional filtration steps to control particle size and molecular weight polydispersity.

TABLE 4

Therapeutic effect of modified pectin samples prepared by previous and new procedures

| Sample ID | Cell Apoptosis Model IC50 µg/mL |
|---|---|
| JR017047-2 | 289 |
| JR017053-2 | Inactive |
| KB027002-9 | 43 |
| KB027002-8 | Inactive |
| BB023013-10 | 34 |
| 6612 | 67 |

Figure 4:
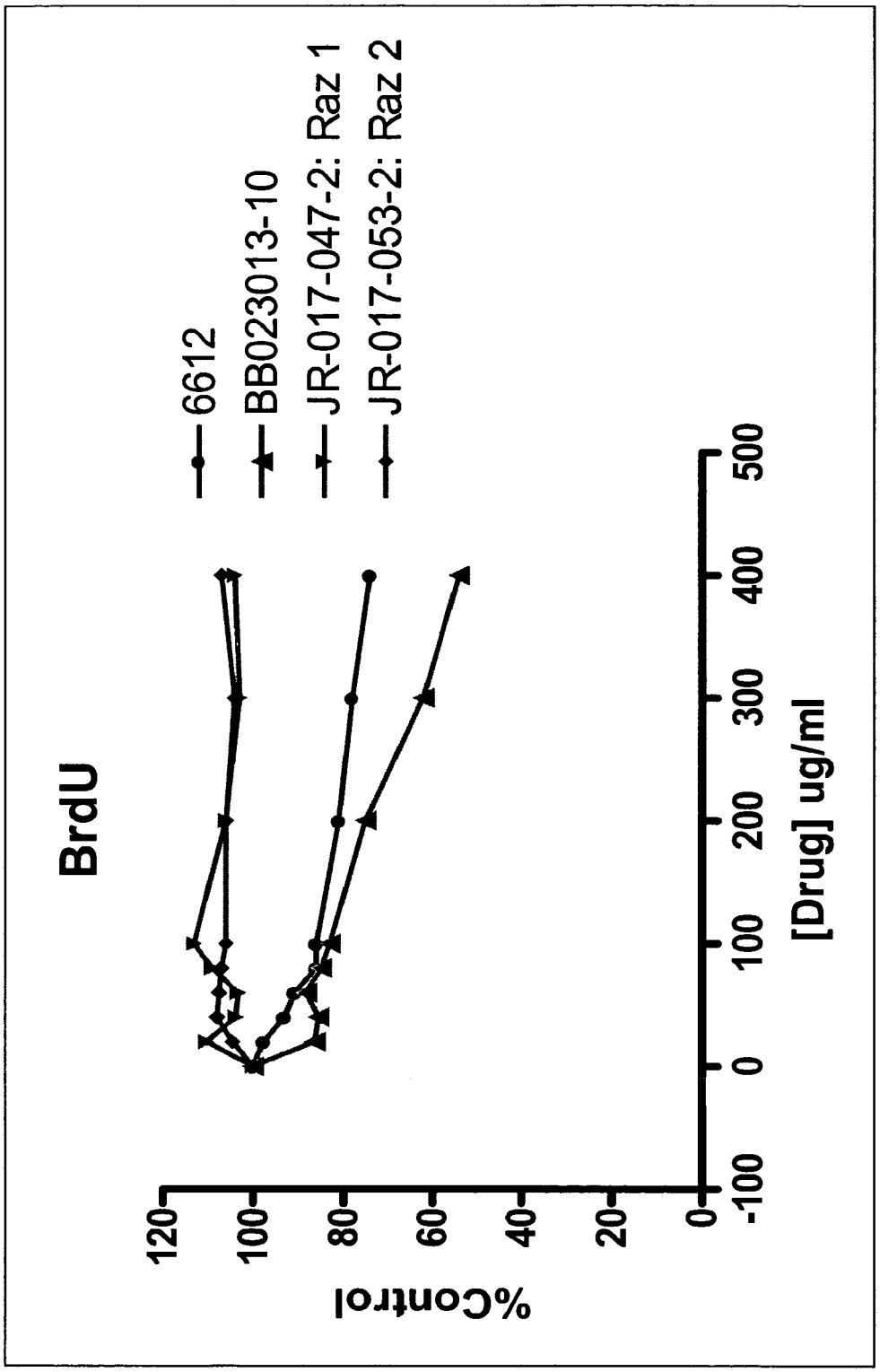
FIG. 4 demonstrates the effect of modified pectin prepared by prior and new methods on DNA synthesis inhibition.

FIG. 4 show the DNA synthesis inhibition testing results for the four compounds tested (as outlined above). Like the Cell Apoptosis model, this data clearly shows the improved therapeutic effectiveness of the modified pectin that can be achieved as a result of using the methods of the current invention. When the cells that have been treated by the 6612 sample was washed and re-seeded in a medium free of modified pectin, the DNA synthesis level returned to that of the control, indicating that the inhibition of DNA synthesis by the presence of 6612 is reversible.

All references cited within the specification are incorporated by reference in their entireties. The foregoing discussion and description is illustrative of specific embodiments, but is not meant to be a limitation upon the practice thereof. It is the following claims, including all equivalents, which define the scope of the invention.

We claim:

1. A composition comprising a colloidal solution of a purified modified pectin or a deesterified, partially depolymerized and purified modified pectin, wherein the colloidal solution comprises colloidal particles less than 1 micron in diameter that consist essentially of a purified modified pectin or a deesterified, partially depolymerized and purified modified pectin having an average molecular weight in the range of 70 to –175 kD.

2. The composition of claim 1, wherein the average molecular weight of the modified pectin or deesterified and partially depolymerized modified pectin is from 80-150 kD.

3. The composition of claim 2, wherein the average molecular weight of the modified pectin or deesterified and partially depolymerized modified pectin is from 80-100 kD.

4. The composition of claim 1, wherein the average molecular weight of the modified pectin or deesterified and partially depolymerized modified pectin is from 70-150 kD.

5. The composition of claim 1, wherein the composition is substantially free of modified pectins having molecular weights below 25 kD.

6. The composition of claim 1, wherein the composition is an aqueous solution.

7. The composition of claim 6, wherein the solution contains at least 0.5% by weight of the modified pectin or deesterified and partially depolymerized modified pectin.

8. The composition of claim 7, wherein the solution contains at least 5% by weight of the modified pectin or deesterified and partially depolymerized modified pectin.

9. The composition of claim 1, wherein the modified pectin or deesterified, partially depolymerized modified pectin is prepared by passing an aqueous solution of modified or unmodified pectin through a tangential flow filter.

10. The composition of claim 9, wherein the aqueous solution of modified or unmodified pectin is prepared by sequentially subjecting an aqueous pectin solution to alkaline conditions and acidic conditions in either order.

11. The composition of claim 1, wherein the colloidal particles are less than 0.20 µm in diameter.

12. The composition of claim 1, wherein the composition comprises a purified modified pectin.

13. The composition of claim 1, wherein the composition comprises a purified deesterified and partially depolymerized modified pectin.

14. The composition of claim 1, wherein the modified pectin or deesterified and partially depolymerized modified pectin inhibits cancer proliferation with an $IC_{50}$ less than 200 µg/mL.

15. The composition of claim 14, wherein the modified pectin or deesterified and partially depolymerized modified pectin inhibits cancer proliferation with an $IC_{50}$ in the range of 25-75 µg/mL.

16. A pharmaceutical composition comprising a pharmaceutically acceptable excipient and the composition of claim 1.

17. A dosage form comprising a composition of claim 1, wherein the dosage form is selected from dosage forms suitable for oral administration, topical administration and inhalation.

18. The dosage form of claim 17, wherein the dosage form is suitable for oral administration.

19. A dosage form comprising a composition of claim 1, wherein the dosage form is suitable for parenteral administration.

20. The dosage form of claim 19, wherein the parenteral administration is selected from injection or intravenous infusion.

21. A method of administering a composition of claim 1 to a patient in need thereof, comprising parenterally administering the composition to the patient.

22. A method of administering a composition of claim 1 to a patient in need thereof, comprising orally administering the composition to the patient.

* * * * *

UNITED STATES PATENT AND TRADEMARK OFFICE
CERTIFICATE OF CORRECTION

| | |
|---|---|
| PATENT NO. | : 8,420,133 B2 |
| APPLICATION NO. | : 13/588877 |
| DATED | : April 16, 2013 |
| INVENTOR(S) | : Staples et al. |

It is certified that error appears in the above-identified patent and that said Letters Patent is hereby corrected as shown below:

In the Claims:

At column 26, claim number 1, line numbers 19 and 20, please replace "in the range of 70 to - 175 kD" with --in the range of 70 to 175 kD--.

Signed and Sealed this
Thirteenth Day of May, 2014

Michelle K. Lee
*Deputy Director of the United States Patent and Trademark Office*